United States Patent [19]

Matthews

[11] Patent Number: 4,776,347
[45] Date of Patent: Oct. 11, 1988

[54] DEVICE FOR DEVLOPING CONTROL OF SPINCTER-TYPE MUSCLES

[75] Inventor: Howard V. Matthews, Sussex, England

[73] Assignee: E. R. Squibb & Sons, Inc., Princeton, N.J.

[21] Appl. No.: 256,416

[22] Filed: Apr. 22, 1981

[30] Foreign Application Priority Data

May 20, 1980 [GB] United Kingdom ............. 8016613

[51] Int. Cl.$^4$ ............................................. A61M 25/00
[52] U.S. Cl. ................................... 128/774; 604/96; 604/99; 604/100
[58] Field of Search ............... 128/774–780, 128/348–350, 748; 604/96–100

[56] References Cited

U.S. PATENT DOCUMENTS

| | | | |
|---|---|---|---|
| 2,458,305 | 1/1949 | Sanders | 128/348 |
| 2,507,858 | 5/1950 | Kegel | 128/2 |
| 2,541,520 | 2/1951 | Kegel | 128/2 |
| 2,638,093 | 5/1953 | Kulick | 128/133 |
| 3,502,328 | 3/1970 | Hamilton | 272/80 |
| 3,598,106 | 8/1971 | Buning | 128/2 |
| 3,646,929 | 3/1972 | Bonnar | 128/1 |
| 3,726,273 | 4/1973 | Cole | 128/2 |
| 3,752,150 | 8/1973 | Harris | 128/2 |
| 3,926,178 | 12/1975 | Feldzamen | 128/2 |
| 4,048,985 | 9/1977 | Sasse | 128/2 |
| 4,050,449 | 9/1977 | Castellana et al. | 128/2 |
| 4,133,303 | 1/1979 | Patel | 128/774 |
| 4,149,539 | 4/1979 | Cianci | 128/350 R |
| 4,167,938 | 9/1979 | Remih | 128/778 |
| 4,216,783 | 8/1980 | Kaiser et al. | 128/778 |
| 4,230,102 | 10/1980 | Ekbladh | 128/349 R |
| 4,325,387 | 4/1982 | Helfer | 128/778 |

FOREIGN PATENT DOCUMENTS

| | | | |
|---|---|---|---|
| 790091 | 11/1935 | France | 128/780 |
| 81-02098 | 8/1981 | PCT Int'l Appl. | 128/774 |
| 808867 | 2/1959 | United Kingdom . | |
| 1303559 | 1/1973 | United Kingdom . | |
| 1399093 | 6/1975 | United Kingdom . | |
| 1511557 | 5/1978 | United Kingdom . | |
| 1547328 | 6/1979 | United Kingdom . | |
| 2047539 | 12/1980 | United Kingdom . | |

OTHER PUBLICATIONS

Kegel, "Physiologic Therapy for Stress Incontinence", JAMA, vol. 146, 915–917, (1951).
Jones, "Nonoperative Treatment of Stress Incontinence", Clin. Obstet. & Gynec., vol. 6, 220–235 (1965).

Primary Examiner—Nancy A. B. Swisher
Attorney, Agent, or Firm—Lawrence S. Levinson; Stephen B. Davis

[57] ABSTRACT

The device comprises a substantially cylindrical support member which carries or in part defines an inflatable cuff. The cuff extends for only a portion of the length of said support member. Means are provided for inflating the cuff with air and transmitting changes in pressure within the cuff to a display device such as a pressure gauge.

3 Claims, 2 Drawing Sheets

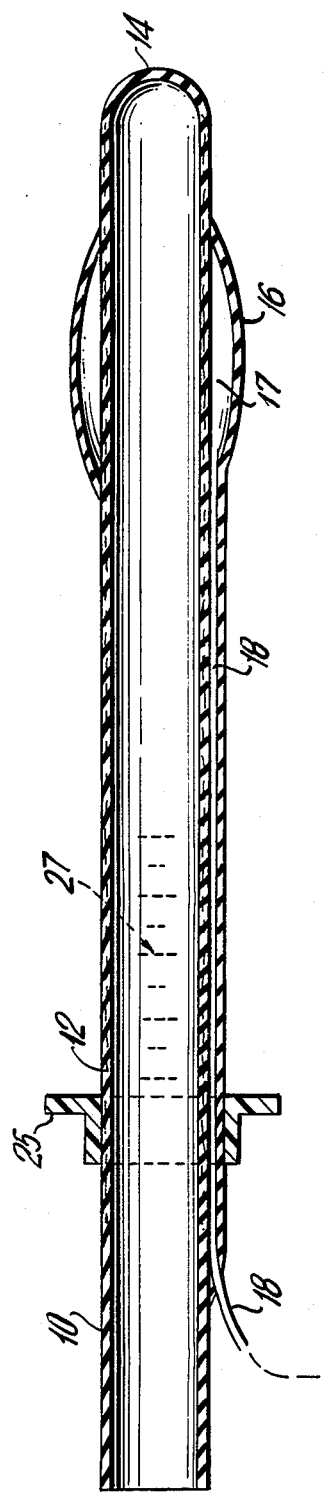
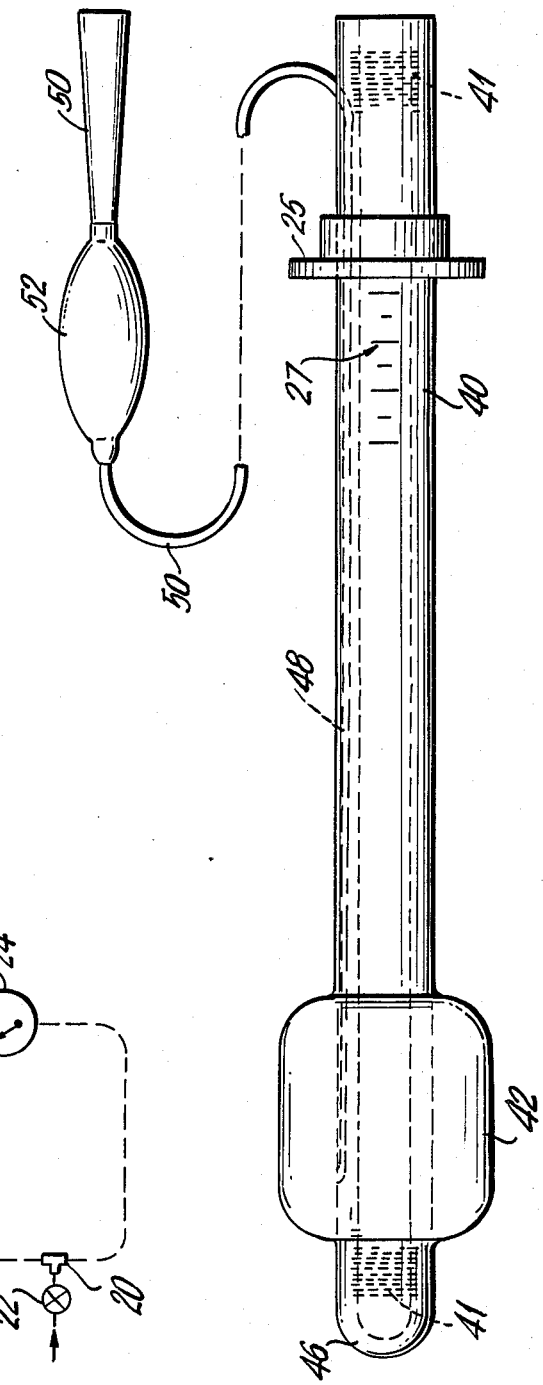
FIG. 1
FIG. 2

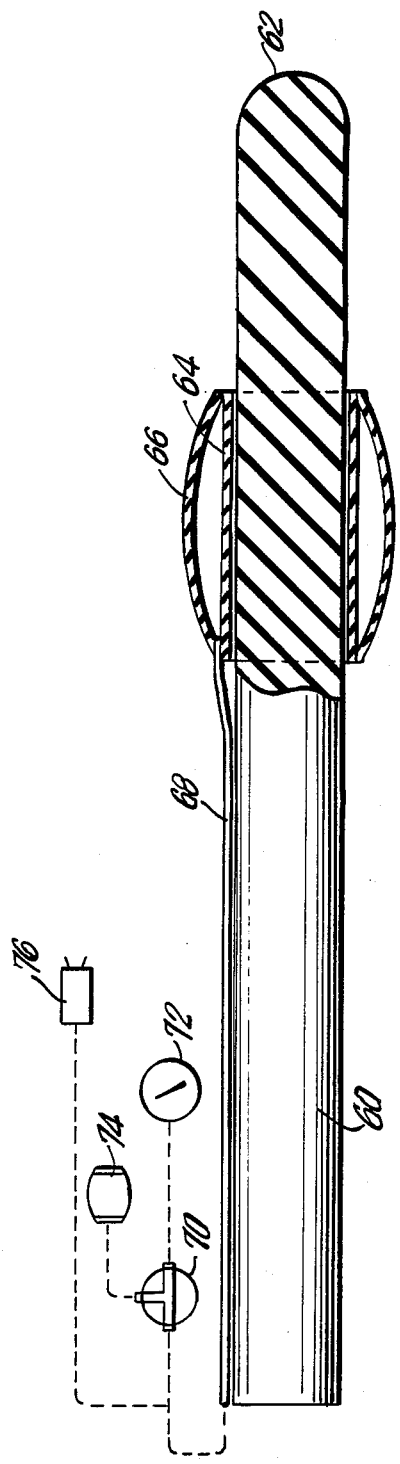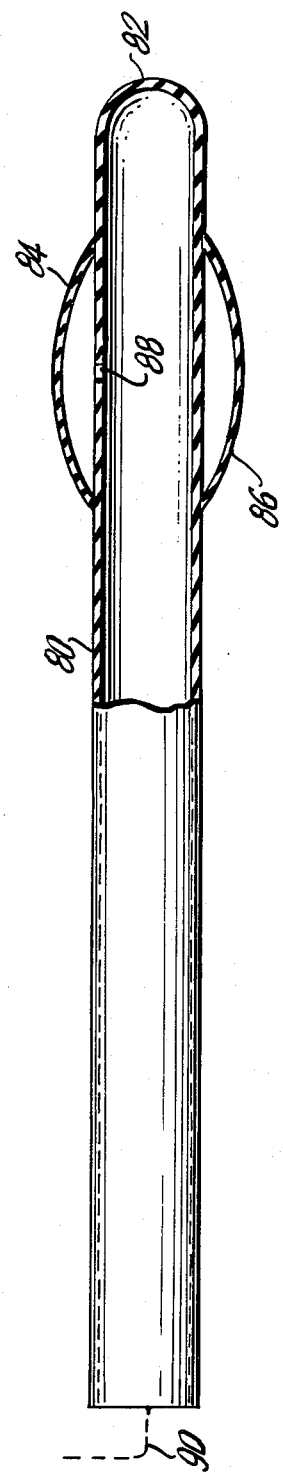

DEVICE FOR DEVLOPING CONTROL OF SPINCTER-TYPE MUSCLES

BACKGROUND OF THE INVENTION

Devices have been proposed for exercising sphincter-type muscles. For example, Kegel in U.S. Pat. Nos. 2,507,858 and 2,541,520 employs a device having a core and a laterally extending vulcanized rubber disc which forms a stop to limit the extent of insertion. A flexible and expansible bulb surrounds the core. In use the device is inserted up to the stop and the bulb is inflated to bring its wall into engagement with the wall of the muscle of interest. A pressure guage connected to the interior of the bulb is then used to monitor compression of the bulb achieved by the efforts of the user in intentionally contracting the muscle of interest. This device has achieved a certain amount of practical use but it is not popular among users because it is uncomfortable to insert and to use and the results obtained often are not sufficiently specific to a particular muscle of interest.

Other devices for exercising sphincter-type muscles are disclosed by Hamilton in U.S. Pat. No. 3,502,328, by Buning in U.S. Pat. No. 3,598,106, by Cole in U.S. Pat. No. 3,726,273, by Harris in U.S. Pat. No. 3,752,150, by Feldzamen in U.S. Pat. No. 3,926,178, by Sasse in U.S. Pat. No. 4,048,985, by Castellana et al. in U.S. Pat. No. 4,050,449, by Remich in U.S. Pat. No. 4,167,938, by Kaiser et al. in U.S. Pat. No. 4,216,783 and by Sokol in British Pat. No. 808,867.

SUMMARY OF THE INVENTION

The device of this invention comprises a substantially cylindrical elongated support member which carries or in part defines an inflatable cuff. The cuff extends longitudinally less than one quarter the length of the support member. Means are provided for inflating the cuff with a fluid such as a gas, preferably air, and for transmitting changes in pressure in the fluid within the cuff to a display device such as a pressure guage.

The elongated support member also carries a flange optionally adjustable along the length of the member. The elongated member may also have markings or graduations so that the flange position can be noted when the device is first inserted, for example by a medical practitioner, who will be able to locate the cuff properly in relation to the particular muscle whose tone is to be elevated or improved. The user is then able to employ the device without the presence of the medical practitioner, having noted the flange position, secure in the knowledge that the muscle of interest and not an adjacent muscle is being monitored and exercised.

Thus, for a female patient with urinary incontinence, the flange will be placed in contact with the external surfaces of the labia majora and the member adjusted to correctly locate the cuff relative to the pubococcygus muscle.

BRIEF DESCRIPTION OF THE DRAWINGS

FIG. 1 illustrates one example of a device according to the invention,

FIG. 2 illustrates a second example of a device in accordance with the invention, FIG. 3 illustrates a third example of a device according to the invention, and FIG. 4 illustrates a fourth example of a device according to the invention.

DETAILED DESCRIPTION OF THE INVENTION

This invention relates to a device for assisting a person to exercise and strengthen and improve his or her control of certain internal muscles herein called sphincter-type muscles.

In this specification, the term "sphincter-type muscle" is used to mean any internal muscle in the human body which plays a part in controlling the excretory functions. Examples are the anal sphincter muscle and the levatores ani group of muscles of the pelvic floor, in particular the pubococcygeus muscle.

Certain conflicting requirements desirably should be met in a device of this kind which is intended for home use by relatively unskilled and non-medical persons. Firstly, the device must be stiff enough to insert to the required distance, without it collapsing. Secondly, the device must be of a shape and surface texture that is easily and comfortably inserted. Thirdly, it must be sensitive enough to clearly register muscle movements on a display unit such as a pressure guage even though only a very slight muscle movement may have taken place.

The device of this invention by having an inflatable cuff of limited longitudinal (i.e., axial) extent enables the user to monitor a particular selected muscle. The device is very sensitive to slight muscle movements as a result of the relatively small internal volume of the cuff. Thus, small changes in the volume of the cuff register as a significant proportional change in the pressure reading on the guage.

According to a particular embodiment of the invention, the device includes a tube with one closed and one open end forming a support member and having an inflatable cuff near the closed end, a second tube opening into the interior of the inflatable cuff, a pressure guage attached to the other end of the second tube, and a valve whereby air or gas can be allowed to enter the second tube in order to inflate the cuff. The tube may be made of latex rubber reinforced over a major part of its length with fibre or cord so as to impart the required stiffness to the tube.

In a preferred version of the invention, the inflatable cuff is formed by an internal wall constituted by part of the support member and an external wall which is freely stretchable. The stretchable wall may be formed of thin latex rubber. A conduit through which the cuff is inflated may be formed by a second tube or by the hollow center of the tube constituting the support member.

In an alternative embodiment of the invention, the inflatable cuff may be formed by a hollow annular member of substantially toroidal or "doughnut" shape, slidable along the length of the elongated support member. The interior of the cuff is then connected to a conduit so that initially the cuff can be inflated and thereafter the changes in internal pressure therein produced by spincter-type muscle movement can be monitored by a pressure guage.

Referring to FIG. 1, a rubber tube 10 has reinforcement 12 over most of its length, and has a rounded closed end 14. An inflatable cuff 16 is located near the end 14 and a second tube 18 is in communication with the interior 17 of the cuff. The tube 18 is connected to a T-piece 20 which is in turn connected to a valve 22 and a pressure guage 24. The tube 10 has a flange 25 slidable along it which enables the user to locate the device in the same position each time it is used. As an optional refinement, graduations 27 may be marked on the tube 10 so that the user can note the position of the flange 25 when the cuff 16 is properly located relative to the muscle being exercised. The tube 10 is preferably made of latex rubber by a dipping process and may be amalgamated by this dipping process with the second and thinner latex tube 18.

Referring now to FIG. 2, the illustrated device includes a first tube 40 and a floppy cuff 42. An inflation lumen 48 is provided in the tube 40 and opens into the interior of cuff 42 near its distal end. The lumen 48 is directly connected to an external thin tube 50 incorporating a test balloon 52. This gives a visual indication to the user because it is distended when the cuff is inflated. The tube 50 leads to a valve and pressure guage in same way as illustrated in the FIG. 1 embodiment.

The tube 40 can be of rubber latex formed by dipping and including a nylon cord reinforcement 41 wound at about 24 turns per 25 mm. of tube length. This reinforcement embedded in the tube wall prevents collapse of the tube 40 during insertion. The floppy cuff 42 can be a thin rubber latex wall and may have an axial length of about 40 mm. The distal end of cuff 42 may be spaced about 20 mm. from the closed distal end 46 of tube 40. The tube 40 may typically have an inner diameter of about 9 mm. and an outer diameter of about 16 mm., and an overall length of about 220 mm. The reinforcement 41 may extend over the length of tube 40 except for about 10 mm. at the distal end.

Tubes 10 and 40 can be made of materials other than rubber. For example, synthetic polymeric materials such as polyvinylchloride or polyurethane with nylon or metal wire reinforcement may be employed.

The device illustrated in FIG. 3 consists of a substantially cylindrical solid rubber or plastics mandrel 60 with a rounded end 62. Typically, the mandrel may be about 150 mm. to about 220 mm. in length and of a diameter of about 9 mm. to about 12 mm. The mandrel 60 carries a sleeve 64 of rubber or plastics material which is slidably mounted thereon. Sleeve 64 has a thin flexible and extensible latex rubber wall 66 fixed to it in an air-tight fashion. Sleeve 64 and wall 66 together define an inflatable cuff to the interior of which is connected a thin-walled tube 68. The tube 68 may be suitably fastened to the mandrel 60, in such a way as to allow slidable movement of the cuff along the mandrel. The tube 68 is connected to a T-piece and valve 70 and then alternatively to a pressure guage 72 or a manually operable inflater bulb 74. An advantage of this construction is that the inflatable cuff can readily be moved along the mandrel 60, nearer to or further from the end 62, as may be required to position it appropriately in relation to the muscle whose performance is to be monitored. A pressure relief valve 76 prevents a pressure greater than a predetermined limit being built up in the cuff 64, 66, even if the bulb 74 is continuously operated.

The device illustrated in FIG. 4 includes a hollow rubber latex tube 80 with a rounded end 82, its wall being of appropriate thickness or suitably reinforced (for example as described with reference to the device of FIGS. 1 and 2) to give the device a stiffness so that it can be readily inserted without discomfort and yet has sufficient rigidity not to be deformed by the muscle movements being monitored. The tube 80 has a thin flexible and expansible annular rubber latex wall 84, similar to the wall 16 of FIG. 1, defining with the tube 80 an inflatable cuff 86. A hole 88 is provided in the wall of the tube 80 leading into the interior of the annular cuff 86. The interior of the tube 80 is connected by a line 90 to a T-piece and valve, bulb, pressure relief valve and guage (all not shown) in the same way as illustrated in FIG. 3.

Although not shown in FIGS. 3 and 4, a flange corresponding to the flange 25 in FIG. 1, slidable along the tube, is preferably included in the arrangements shown in FIGS. 3 and 4.

Pressure gauge 24 (or 72) may be mechanical, electrical, or electronic. A muscular contraction will show as an increase in pressure of about 1 to 8 mm. of mercury on the gauge, and so will be clearly noticeable to the patient.

The pressure gauge may be an electronic pressure sensor unit capable of giving either a numerical display of pressure value or a display of lights, for example of different colors, triggered by the achievement of certain pressure valves. For example, with such a unit it could be arranged using suitable circuity that a given muscle contraction (and hence a given pressure) illuminates a lamp of one color, a greater contraction illuminates a lamp of a second color, and a greater contraction still illuminates a lamp of a third color. Such a unit would preferably include a means of controlling the sensitivity so that the particular levels of pressure at which given lamps are illustrated could be adjusted.

For improved sensitivity, it is preferred that tube 18 or tubes 50 and 48 or tube 68 be thin. For example, the tube may have an inner diameter of about 0.5 to about 1.5 mm.

The devices of this invention are employed as follows. The device is inserted into the body orifice to the desired depth as determined by flange 25. The valve 22 or 72 is opened and the cuff is inflated in any convenient way to a light pressure, for example about 40 to 60 mm. of mercury. The valve is closed and the patient then attempts to contract the sphincter muscles. The resultant efforts show clearly on the pressure gauge.

What is claimed is:

1. A device for assisting a person to exercise and improve control of sphincter type muscles consisting of a substantially cylindrical tube having a closed rounded distal end, an inflatable cuff supported by said cylindrical tube and located near said rounded distal end, said cuff having a longitudinal extent which is less than one quarter of that of said cylindrical tube, a thin second tube having one end which opens into the interior of said cuff, the other end of said second tube being attached to a pressure guage and a valve whereby air or gas can be allowed to enter said second tube and inflate said cuff and whereby changes in pressure in the air of gas within said cuff are displayed on said pressure guage, siad cylindrical tube including a series of graduations or markings, and a flange serving as a location device carried by and adjustable along the length of said cylindrical tube so as to enable the user to locate the cuff properly in relation to the particular muscle whose tone is to be elevated or improved.

2. A device according to claim 1 in which said cylindrical closed ended tube is formed of rubber latex which is reinforced over a major portion of its length.

3. A device according to claim 2 in which said cylindrical closed ended tube is amalgamated with said second tube by a latex dipping operation.

* * * * *